United States Patent [19]

Perlberg

[11] Patent Number: 4,547,360
[45] Date of Patent: Oct. 15, 1985

[54] METHOD AND COMPOSITIONS FOR REPELLING PESTS

[75] Inventor: William Perlberg, Wyckoff, N.J.

[73] Assignee: The Hartz Mountain Corporation, Harrison, N.J.

[21] Appl. No.: 661,867

[22] Filed: Oct. 16, 1984

Related U.S. Application Data

[63] Continuation of Ser. No. 457,944, Jan. 14, 1983, abandoned.

[51] Int. Cl.[4] .................... A01N 37/34; A01L 9/04
[52] U.S. Cl. ........................... 424/45; 514/521; 514/875; 514/919; 424/DIG. 10
[58] Field of Search ............ 424/304, 45, DIG. 10; 514/521, 875, 919

[56] References Cited

U.S. PATENT DOCUMENTS

| | | | |
|---|---|---|---|
| 3,996,244 | 12/1976 | Fujimoto et al. | 424/275 |
| 4,062,968 | 12/1977 | Fujimoto et al. | 424/275 |
| 4,238,406 | 12/1980 | Suzuki et al. | 424/304 |
| 4,366,777 | 1/1983 | Akhavein et al. | 119/156 |

OTHER PUBLICATIONS

Dinet et al., C.A., vol. 96, (1982), 212511z.
Garson et al., J. Med. Ent. 5, 339-352, (1968).
Dethier, Ann. Ren. Ent. 1, 181-202, (1956).
Roadhouse, Canadian J. Zool. 31, 535-546, (1953).
Travis, J. Natl. Malar. Sci. 6, 180-183, (1947).
Bar-Zeev et al., Mosquito News 31, 56-61, (1971).
Buescher et al., J. Med. Entomol. 21, 278-282, (1984).

*Primary Examiner*—Allen J. Robinson
*Attorney, Agent, or Firm*—Curtis, Morris & Safford

[57] ABSTRACT

What are disclosed are a method for repelling small blood feeding pests from the skin, hair, or fur of a mammal, which method comprises applying a pest repellant amount of a repellant which is cyano (3-phenoxyphenyl) methyl-4-chloro-alpha-(1-methylethyl) benzeneacetate to said skin, hair, or fur and compositions for performing this method.

11 Claims, No Drawings

METHOD AND COMPOSITIONS FOR REPELLING PESTS

This application is a continuation of application Ser. No. 457,944 filed Jan. 14, 1983, and now abandoned.

The present invention relates to a method for repelling small blood feeding pests from the skin, hair, or fur of a mammal, and to repellant compositions for practicing said method.

More in particular, the present invention relates to a method for repelling pests such as ticks, fleas, and mosquitoes from humans and animals such as cats and dogs, and to repellant compositions for practicing such methods.

At present a number of compositions are on the market which are alleged to repel such small blood sucking pests as ticks and fleas from household pets such as cats and dogs. These compositions, which may be topically applied, such as dips and sprays, or which may be systemic, are in fact insecticidal compositions having little or no repellant effect. Even though such compositions may in due course kill blood feeding pests such as ticks and fleas which are present on an animal, nevertheless they suffer the disadvantage that they permit, or even require, that the pests be present on the animal, at least for the time required for the insecticide to kill. Systemic insecticides further have the disadvantage that, for efficacy, the pests must feed on the animal. Pets are capable of developing allergic reactions to the enzymes excreted by the blood feeding pests to prevent coagulation of the blood on which they feed.

The problem thus existed of finding a composition, suitable to be applied to the skin, hair, or fur of a mammal, for repelling small blood feeding pests of the type described above, particularly ticks, fleas and mosquitoes.

Certainly, effective repellants are known to the art. One of these, N,N-diethyl-m-toluamide (hereinafter DEET) is known to be excellently effective as a mosquito repellant. A number of compositions containing this material are commercially available for use as a repellant on humans and animals, for instance in a form of aerosol compositions. Although DEET is so effective as a repellant that it has been used in studies reported later herein as a standard for testing repellancy, it had the dual disadvantage that it must be used in relatively high concentrations and, more importantly, it is not effective for affording continuous protection against pests for more than about six hours.

According to the present invention, a method has now been found for repelling small blood-feeding pests from the skin, hair, or fur of a mammal by topically applying to the animal a repellant which is cyano(3-phenoxyphenyl)methyl-4-chloro-alpha-(1-methylethyl)-benzeneacetate, of the following formula:

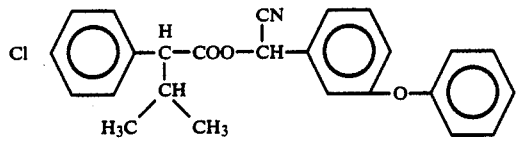

The active compound is conveniently formulated into compositions which are adapted to topical application to the skin, hair, or fur of a mammal, and these compositions are also a feature of the present invention.

The active compound mentioned above and methods for its preparation are known from Fujimoto et al. U.S. Pat. No. 4,062,968. The compound is one of many hundreds of substituted acetate compounds of the general formulae

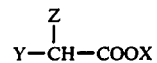

which are taught by the patent to be useful as pesticides, particularly in insecticides and miticides. The pesticides are taught as useful for controlling mosquitoes, flies, cockroaches, grain insects such as the rice weevil, mites, agriculturally obnoxious insects such as planthoppers, green rice leafhoppers, cabbage army worms, diamond-back moths, noctuidae, cabbage worm, rice stem borers, aphids, tortrixes, leaf-miners, and the like. More specifically, the compounds are reported as having selective or non-selective pesticidal activity on such orders as Coreoptera, Lepidoptera, Diptera, Orthoptera, Hemiptera, Homoptera, Acarus, and other pests such as nematoda.

A number of the many pesticidal compounds disclosed in the aforementioned Fujimoto et al. patent are shown in Experimental Example 3 of the patent to have a repellant effect against spider mites (*Tetranychus telarius*) as tested on seedlings of mottled kidney beans treated with an emulsifiable concentrate prepared by blending the compound tested with xylene and "Sorpol SM-200", presumably an emulsifying agent. The compounds tested for repellancy against spider mites do not include the compound used according to the present invention, the common name of which is fenvalerate and which is commercially available under tradenames such as "Pydrin" and "Ectrin". The active compound will be identified hereinafter as "FV" for sake of convenience.

Thus, although FV is known in the art as a pesticide, and compounds related to FV have been shown to have repellant activity for spider mites on plants, one skilled in the art would not have expected from such teachings that FV would have outstanding properties as a repellant for small blood feeding pests such as ticks, fleas, and mosquitoes, particularly the long lasting activity which is observed. Many well known insecticides have no effective repellant properties; conversely, many materials recognized as repellants do not have any pesticidal effect.

In discovering the unique repellant properties of FV, approximately 80 known compounds were tested, of which all were known to have some repellancy for fleas or mosquitoes and over half of which were known to exhibit repellancy activity comparable to or better than that of DEET against biting fleas and/or mosquitoes.

Because of the magnitude of the testing effort, the compounds were first tested for repellant efficacy by an in vitro technique employing the brown dog tick, *Rhipicephalus sanguineus*. Ticks were used for the assay because they are more resistant to pesticides and repellants than are other pests such as fleas or mosquitoes, because they are less mobile than fleas or mosquitoes, and because they need blood feeding three times in their life cycle.

The in vitro test procedure involved weighing each material to be tested and dissolving it in ethanol. Next, 0.15 ml of the test solution was applied to a disk, 2.9 cm in diameter, cut from No. 3 Whatman filter paper. The treated disks were kept under a hood and allowed to dry for 24 hours.

Each treated disk was then mounted in a drilled-out vial cap that the treated side faced down when the cap was placed on a seven dram polystyrene vial (25×52 mm) which served as a test chamber. In each case, an untreated filter paper disk was also glued on the drilled out bottom of the vial. In each case, fifteen holes were punched in both disks when in position on the chamber.

Next, twenty unfed adult brown dog ticks (ten male and ten female), sorted 24 hours before use, were placed in each test chamber. The chambers were held with the treated end upright under a hood. Four hours later, when the ticks had ceased wandering, the chamber was observed and the number of ticks on the treated top surface of the chamber were counted. Because of the known tendency of ticks to climb, the presence of ticks on the treated upper surface of the test chamber indicated a lack of repellancy. In each case, non-treated, standard-treated, and solvent-treated disks were included in the test.

Twenty-six of 81 compounds tested were initially tested at an area concentration of 1.0 mg/cm$^2$ and then again at lower levels if activity was observed. Replica testing was conducting on all but one of these compounds in order better to validate the assay. Subsequent compounds were testes at a lower initial test level of 0.44 mg/cm$^2$. Compounds highly active at this level would be clearly superior to DEET and Indalone (butyl 3,4-dihydro-2,2-dimethyl-4-oxo-2H-pyran-6-carboxylate) used as standards of repellancy. In general, the best conventional repellants (apart from the material of the present invention) were rhodanine and oxo-rhodanine compounds, of which seven compounds tested were more than 75% active at a level of 0.29 mg/cm$^2$ or less. 3-ethyl,5-n-hexyl rhodanine and 3-methyl, 5-n-hexyl rhodanine were found to be 100% repellant at a concentration of 0.13 mg/cm$^2$. In comparison, FV shows comparable high repellant activity down to a level of only 0.005 mg/cm$^2$.

FV was next tested in vivo in an animal host to determine whether the in vitro effect reported above was in fact valid. Also, it was necessary to determine whether the repellancy effect also occurred among fleas, the other main ectoparasite affecting household pets. Because of the mobility of fleas, it was not possible to develop an in vitro evaluation method for these insects.

For in vivo testing, six adult short-haired beagle-sized conditioned mongrel dogs were used as test animals. Two dogs, one treated with a test aerosol and one treated with a control aerosol, are used to evaluate each test material. After treatment, the dogs are released to outdoor runs, allowed to dry for approximately four hours, and then are brought into the testing room.

The testing room is 11.5×11.5 ft. in size with a 2.5×6.5 ft. dog run on two opposite sides of the room. One run is used to house the dog treated with the test material; the control dog is in the second run. Unfed adult cat fleas (Ctenocephalides felis), which are the principal parasitic flea for dogs, were released in the center of the room and 75 unfed adult brown dog ticks were released at the side of each run. The room was sealed and the dogs were left in the test chamber overnight. The next morning, the room was washed and all parasites were removed from the dogs and counted. If a test material was active, the dogs were returned to outdoor runs and rechallenged at periodic intervals following the initial treatment.

Initial trials were made with the active ingredient at a concentration of 0.005 mg/cm$^2$. Since the body surface of the animals tested was approximately 4,000 cm$^2$, approximately 20 mg of FV were applied per dog using an ethanol solution of the chemical and applying with an atomizer. The results are shown in Table 1 below.

TABLE 1

| In Vivo Evaluation At .005 mg/cm$^2$ (20 mg/dog) | | | | | |
|---|---|---|---|---|---|
| | 24 Hour | | 48 Hour | | 8 Days |
| | T | F | T | F | T | F |
| EtOH | 2 | 60 | 37 | 53 | 31 | 57 |
| FV | 0 | 4 | 0 | 5 | 0 | 26 |

T = Ticks;
F = Fleas;
Numbers signify live parasites observed.

Thus, repellancy effect expected with ticks from the in vitro experiments was, in fact, observed also in vivo together with a significantly effective repellancy effect against fleas.

However, to improve the effect and make it longer lasting, the tests were repeated and a concentration of 0.01 mg/cm$^2$ (40 mg FV/dog) and again at 0.02 mg/cm$^2$. The results of the latter experiment are shown below in Table 2, from which it will evident that there is almost complete repellancy of ticks for a period of 22 days as well as more than 80% repellancy of fleas at the end of the same period.

TABLE 2

| | 24 Hours | | 48 Hours | | 6 Days | | 9 Days | | 16 Days | | 22 Days | |
|---|---|---|---|---|---|---|---|---|---|---|---|---|
| | T | F | T | F | T | F | T | F | T | F | T | F |
| EtOH | 13 | 32 | 33 | 102 | 32 | 115 | 60 | 126 | 19 | 81 | 41 | 50 |
| FV | 0 | 0 | 0 | 1 | 0 | 8 | 1 | 1 | 0 | 8 | 1 | 11 |

In a further test to improve upon flea repellancy, the concentration of FV was increased to 0.04 mg/cm$^2$ or 160 mg of FV per dog. In Table 3 below, the results are shown together with the results of crossover tests in which the dogs and treatments were reversed in order to eliminate animal bias. That is, the dog treated with ethanol as a control received the active ingredient in ethanol solution during the crossover experiment, while the dog which had previously received the active ingredient was treated with ethanol in the crossover.

TABLE 3

| | 24 Hours | | 7 Days | | 14 Days | | 21 Days | |
|---|---|---|---|---|---|---|---|---|
| | T | F | T | F | T | F | T | F |
| EtOH | 3 | 45 | 7 | 85 | 11 | 21 | 19 | 68 |
| FV | 0 | 0 | 2 | 0 | 0 | 5 | 1 | 13 |
| | | | Cross over same rate | | | | | |
| EtOH | 4 | 89 | 2 | 66 | 12 | 123 | 7 | 47 |
| FV | 0 | 0 | 0 | 1 | 0 | 13 | 0 | 15 |

For sake of thoroughness, two additional product lots of FV were evaluated by the in vivo tests described above: a similar effect was observed.

From other studies done at the same time, it was determined that the amount of a spray product normally applied to an average size household pet for full coverage is 50–75 gm. Thus, such a product should contain approximately 0.2% of active ingredient in order to deposit 100–150 mg onto the pet. The active ingredient should be included within a carrier suitable for topical application to the skin, hair or fur of the animal. Thus, the product to be applied should contain approximately 0.2% of active ingredient. An aerosol spray formula containing this level of the active ingredient was developed and was shown to be highly effective. The composition of the aerosol product and the results obtained therewith on beagle-sized dogs are given below in Table 4.

TABLE 4

| Formula prepared | 0.2% FV |
| --- | --- |
| | 61.7% Ethanol |
| | 13.1% $CH_2Cl_2$ |
| | 25.0% Propellent A-46 |
| | (Propane/Isobutane) |

Results:

| | 24 Hours | | 7 Days | | 14 Days | | 21 Days | |
| --- | --- | --- | --- | --- | --- | --- | --- | --- |
| | T | F | T | F | T | F | T | F |
| EtOH | 35 | 20 | 43 | 86 | 24 | 82 | 24 | 30 |
| FV Sample #4511 | 0 | 0 | 1 | 7 | 2 | 6 | 21 | 46 |

The in vivo tests reported above were all performed using indoor kennel facilities. As a final test of the efficacy of FV, comparable outdoor test facilities were employed at a location in north Texas using the same product and a similar protocol. The area was selected because its climate is particularly accommodating to fleas and ticks. The results of the outdoor tests are shown below in Table 5.

TABLE 5

| | 24 Hrs. | | 3 Days | | 6 Days | | 9 Days | | 13 Days | | 20 Days | |
| --- | --- | --- | --- | --- | --- | --- | --- | --- | --- | --- | --- | --- |
| | T | F | T | F | T | F | T | F | T | F | T | F |
| No Treat | 26 | 24 | 32 | 27 | 108 | 34 | 125 | 22 | 36 | 44 | 16 | 27 |
| FV Sample 4901 | 1 | 5 | 0 | 2 | 0 | 5 | 0 | 6 | 3 | 38 | 2 | 27 |

Finally, to permit an evaluation of the in vivo results using FV versus the effects of known repellants, an in vivo test of type described above was undertaken indoors using the known repellant DEET at a concentration of 18%. As a control, a placebo free of any repellant material was employed. The results, given in Table 6 below, show that DEET does show early effectiveness against fleas and ticks at this high concentration, but that the effect is not residual.

TABLE 6

| | 24 Hours | | 7 Days | | 14 Days | | 21 Days | |
| --- | --- | --- | --- | --- | --- | --- | --- | --- |
| | T | F | T | F | T | F | T | F |
| DEET | 4 | 8 | 12 | 64 | 33 | 178 | — | — |
| Placebo | 18 | 32 | 3 | 54 | 13 | 18 | | |

All of the in vivo results reported earlier herein involve tests in which the parasites (ticks and fleas) released had a choice of migration to a treated or to an untreated dog. That is, a host was always available which might be more attractive to the parasites. As a further evaluation, in vivo tests were performed using essentially the same protocol but in which both test dogs were treated with the FV product at a concentration of 0.2%. The results are shown in Table 7.

TABLE 7

| | Day 1 | | Day 7 | | Day 10 | | Day 14 | |
| --- | --- | --- | --- | --- | --- | --- | --- | --- |
| | T | F | T | F | T | F | T | F |
| Sample FV 5002 | | | | | | | | |
| Dog 1 | 0 | 0 | 0 | 0 | 0 | 0 | 0 | 0 |

TABLE 7-continued

| | Day 1 | | Day 7 | | Day 10 | | Day 14 | |
| --- | --- | --- | --- | --- | --- | --- | --- | --- |
| | T | F | T | F | T | F | T | F |
| Dog 2 | 0 | 0 | 0 | 0 | 0 | 1 | 0 | 3 |

As is evident from the Table, neither dog became infested under these test conditions. That is, parasites faced with a choice between two treated dogs did not migrate to either animal.

To test the efficacy of FV as a repellant for mosquitoes, approximately 25 to 50 unfed female mosquitoes, newly hatched from larvae, were placed for each test in a screen cage and applied to the shaved abdomen of a guinea pig a fixed interval of time after the shaved skin of the test animal had been treated with a given concentration of FV in an ethanol solution. Several hours after the completion of each test (to permit determination of mosquito mortality), the living and dead mosquitoes were crushed to ascertain if they had a blood meal. The number of mosquitoes fed was used as a measure of repellancy. The number of mosquitoes killed was used as a measure of insecticidal activity. The results are reported below in Table 8.

TABLE 8

| | 2 Hrs. | | 24 Hrs. | | 48 Hrs. | |
| --- | --- | --- | --- | --- | --- | --- |
| | % Fed | % Dead | % Fed | % Dead | % Fed | % Dead |
| EtOH | 64 | 0 | 43 | 0 | 60 | 0 |
| 1% FV | 18 | 53 | 15 | 46 | 56 | 54 |
| 0.1% FV | 20 | 15 | 42 | 0 | — | — |
| .01% FV | 70 | 0 | 52 | 0 | — | — |

The Table shows that the repellant properties of FV persist at low concentrations at which insecticidal activity is reduced. However, the repellant effect for mosquitoes is more fugitive than for fleas or ticks, at least under the test protocol employed.

As mentioned earlier herein, the active ingredient found to be so highly effective as a repellant according to the present invention can be incorporated in any carrier suitable for application to the skin, hair, or fur of a mammal, particularly household pets and humans.

Thus, a further aerosol product was formulated to decrease flammability and to provide a cosmetically acceptable spray pattern. The composition of the aerosol product is given below in Table 9. It is noted that vitamin E may be added to the composition as a skin emollient, if desired.

TABLE 9

| % | Ingredients | |
| --- | --- | --- |
| 0.2 | FV | Vitamin E may |
| 37.7 | $CH_2Cl_2$ | also be added as |
| 20.4 | Mineral Spirits | skin emollient. |
| 8.4 | Isopropanol | |
| 1.0 | Propylene Glycol | |
| 0.3 | Perfume | |
| 32.0 | Propellent A-46 (Propane/Isobutane) | |
| 100.0 | | |

Alternatively, the active ingredient may be dispensed in the form of a powdered product in an appropriate carrier, for example. A number of compositions containing the active ingredient at various levels are reported below in Table 10.

TABLE 10

|  | A (%) | B (%) | C (%) | D (%) |
| --- | --- | --- | --- | --- |
| FV | 1.0 | 5.0 | 1.0 | 5.0 |
| Isopropanol | 1.0 | 3.0 | | |
| Calcium Carbonate | 48.5 | 41.0 | | |
| Diatomaceous Earth | 49.0 | 40.5 | | |
| Colloidal Silica | 0.5 | 0.5 | 0.5 | 0.5 |
| Talc | — | — | 98.5 | 94.5 |

Finally, Table 10 below gives a formulation which can be conveniently dispensed from a pump-spray unit. It is noted that perfume, propylene glycol, color, and emollients and conditioners may be added to the composition if desired.

TABLE 11

| Pump Spray Repellent | |
| --- | --- |
| FV | 0.2 |
| Isopropanol | 50.0 |
| Water | 49.8 |

It should be clear that the exemplified aerosol, powder, or pump-spray formulations specifically reported herein are merely typical of others which can be formulated (e.g. towlettes, foams, creams, etc.) and that the present invention includes still other formulations, or formulations of the type shown wherein the nature of the ingredients and/or their concentration, including the concentration of the active ingredient, may be varired if desired to conform the product to particular needs.

What is claimed is:

1. A method for repelling ticks, fleas, or mosquito pests from the skin, hair, or fur of a mammal, which method comprises applying a pest repellant amount of a repellant which is cyano(3-phenoxyphenyl)methyl-4-chloro-alpha-(1-methylethyl)benzeneacetate to said skin, hair, or fur.

2. A method as in claim 1 for repelling a tick or flea.

3. A method as in claim 1 for repelling a mosquito.

4. A method as in claim 1 wherein said repellant is applied to said skin, hair, or fur as an aerosol composition.

5. A method as in claim 1 wherein said repellant is applied to said skin, hair, or fur as a powder composition.

6. A method as in claim 1 wherein said repellant is applied to said skin, hair, or fur as a liquid composition.

7. A method as in claim 1 wherein said repellant is applied to said skin, hair, or fur at a minimum area concentration of about 0.005 mg/cm$^2$.

8. A method for repelling ticks or fleas from a dog or cat, which method comprises applying to said dog or cat a repellant amount of a repellant which is cyano(3-phenoxyphenyl)methyl-4-chloro-alpha-(1-methylethyl)benzeneacetate.

9. A method as in claim 8 wherein said repellant amount is at least about 0.005 mg/cm$^2$.

10. A method as in clain 8 wherein said repellant amount is at least about 0.02 mg/cm$^2$.

11. A method as in claim 8 wherein said repellant amount is at least about 0.04 mg/cm$^2$.

* * * * *